(12) United States Patent
Abramov (10) Patent No.: US 9,126,033 B2
(45) Date of Patent: Sep. 8, 2015

(54) BATTLEFIELD DEFIBRILLATION SYSTEM

(71) Applicant: Igor Abramov, Vista, CA (US)

(72) Inventor: Igor Abramov, Vista, CA (US)

( * ) Notice: Subject to any disclaimer, the term of this patent is extended or adjusted under 35 U.S.C. 154(b) by 0 days.

(21) Appl. No.: 14/218,157

(22) Filed: Mar. 18, 2014

(65) Prior Publication Data

US 2014/0288573 A1 Sep. 25, 2014

Related U.S. Application Data

(60) Provisional application No. 61/804,598, filed on Mar. 22, 2013.

(51) Int. Cl.
*A61N 1/39* (2006.01)
*A61N 1/05* (2006.01)

(52) U.S. Cl.
CPC ............. *A61N 1/0587* (2013.01); *A61N 1/0504* (2013.01); *A61N 1/39* (2013.01); *A61N 1/0563* (2013.01)

(58) Field of Classification Search
CPC ....... A61N 1/046; A61N 1/0563; A61N 1/39; A61N 1/0587; A61N 1/0504

USPC .................................... 607/5, 115, 142, 145
See application file for complete search history.

(56) References Cited

U.S. PATENT DOCUMENTS

| 6,560,473 | B2* | 5/2003 | Dominguez | 600/382 |
|---|---|---|---|---|
| 2004/0186545 | A1* | 9/2004 | Rosero et al. | 607/119 |
| 2005/0288716 | A1* | 12/2005 | Zsigmond | 607/5 |
| 2010/0042137 | A1* | 2/2010 | Oronsky et al. | 606/204 |
| 2014/0288574 | A1* | 9/2014 | Abramov | 606/129 |

\* cited by examiner

*Primary Examiner* — Christopher D Koharski
*Assistant Examiner* — Michael Carey (57) ABSTRACT

Several embodiments of a battlefield defibrillation system (2) comprising external defibrillator (6) and at least one electrode (8) connected thereto are described. The system includes direct cardiac access (8), or indirect subcutaneous electrodes (30). The direct cardiac access electrodes (26) engage the heart muscle directly via the intercostal space. Indirect subcutaneous electrodes are positioned under patient's skin. Several design features are implemented to aid precise electrode positioning and facilitate system operation by an untrained personnel.

11 Claims, 8 Drawing Sheets

BATTLEFIELD DEFIBRILLATION SYSTEM

CROSS-REFERENCE TO RELATED APPLICATION

This application claims the benefit of Provisional Patent Application Ser. No. 61/804,598 filed 2013 Mar. 22

FIELD OF INVENTION

This invention relates in general to cardiac defibrillators, and in particular to external portable defibrillators and systems.

BACKGROUND OF INVENTION

Modern medical care in the forward battlefield environment strives to provide the most advanced and timely diagnosis and treatment to casualties possible, since time factor is often crucial to the successful clinical outcomes.

One of the trauma encountered in the battlefield is cardiac ventricular fibrillation (VF) which is invariably fatal unless treated promptly. The common way to treat VF is to administer an electric pulse to the heart which shocks the heart muscle and induces it to revert to normal contraction pattern. This procedure is called defibrillation and is effected by an apparatus called 'defibrillator'.

There are two types of defibrillators: the external and internal, the latter implanted into a patient's body. External defibrillators are relatively large and contain a large battery pack and a high voltage generator. The weight of an external defibrillator is in the order of 2-3 lbs (1-1.5 kg). The generated high voltage pulse is administered to a patient via two large conductive paddles positioned on his chest and side, respectively.

The implantable defibrillator, being very small and light is permanently surgically implanted into a patient's body, and its electrical lead is inserted into the heart. The outer case of the device is made of metal and acts as a second electrode to complete the path of electrical current through the heart. The implantable defibrillators are used in patients with chronic cardiac disease and their implantation requires a major surgery procedure in a hospital setting.

In a forward battlefield environment obtaining an external defibrillator on a short notice is problematic, since due to its size and weight it presents a carry challenge to field medical personnel who are frequently over-burdened with equipment. On the other hand, to implant a defibrillator under field conditions and within an extremely short 'window of opportunity' is not feasible.

Still, having a defibrillation capability 'on-hand' in a forward battlefield environment is very desirable in view of its potential in saving lives.

OBJECTIVES OF THE INVENTION

Thus, it is the objective of instant invention to provide a small and light defibrillator system which can be easily carried by a field military medic along with other first-aid equipment.

Another objective is to provide a defibrillator which would be easy to use even by an untrained personnel.

SUMMARY OF THE INVENTION

In accordance with the present invention, a miniature battlefield defibrillation system is described. The system consists of a small external defibrillator equipped with direct cardiac access-, or indirect subcutaneous electrodes. The direct cardiac access electrodes engage the heart muscle directly, preferably via the left $5^{th}$ intercostal space. Several design features are implemented to aid precise electrode positioning and facilitate system operation by an untrained personnel.

The subcutaneous-type electrodes are positioned below the skin near the patient's sternum and laterally below the left armpit. Their design also facilitates simplified operation by an untrained personnel.

PRIOR ART

The prior art is comprised by two distinct groups of defibrillators: the external and the implantable ones. The external ones, as was mentioned, are large and heavy for the wide use in the forward battlefield environments. The implantable defibrillators, while very small, are unsuitable in the first-response situations.

OBJECTS AND ADVANTAGES

In contrast to the prior art mentioned hereinabove, the present invention provides a miniature external defibrillator, which, together with the specific electrode system delivers the desired defibrillation action.

My research showed that a great difference exists between the required defibrillation energy while using an external defibrillator and using an implanted defibrillator. An external defibrillator is required to deliver up to 400 Joules of electrical energy per pulse. The need for high energy output for external defibrillation results in large size and weight of the corresponding defibrillators. In contrast, only 10-50 Joules per pulse are delivered by an implanted defibrillator with a direct intra-cardiac electrode, with satisfactory defibrillation results.

I determined that the difference in the required pulse energies is due to the high impedance of the human skin and tissues immediately underneath it, which needs to be overcome by the existing external defibrillators in order to deliver sufficient defibrillation energy to the heart.

If, however, the heart can be stimulated from within the body, such as done presently with implanted defibrillators, directly to/inside the heart, or from under the skin and thus avoiding its high impedance, the required pulse energy is greatly reduced.

Thus, it is possible to use a small external defibrillator if its energy is delivered directly to the heart or indirectly subcutaneously, avoiding high losses in the skin and the immediate underlying tissue.

Indeed, an implantable defibrillator, Model S-ICD® introduced recently by Boston Scientific, Inc. of Natick, Mass., USA utilizes an indirect subcutaneous electrode positioned along the sternum, with the defibrillator itself implanted laterally, below left armpit. The metal case of this defibrillator serves as a second subcutaneous electrode to complete the current path through the patient's heart. The energy generated by this device is relatively low 80 Joules per pulse but it is sufficient for successful defibrillation. This further supports the low-impedance model of subcutaneous electrode operation.

Furthermore, in case of external defibrillators, the external electrode pads by necessity are made quite large in order to decrease impedance and current density and avoid burns to the patient's skin. In case of subcutaneous electrodes, this requirement is reduced due to lower impedance.

Nevertheless, in several embodiments of the instant system, precautions were taken to decrease current density at electrodes to minimize a chance of an electrical burn injury to the patient.

DESCRIPTION OF THE PREFERRED EMBODIMENT

In the foregoing description like components are referenced by the like numerals.

Figure 1:
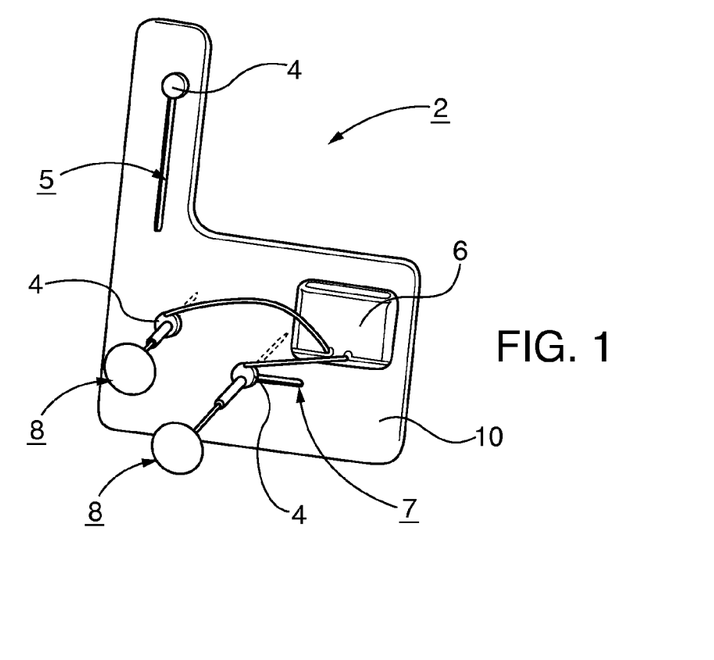
FIG. 1 is a perspective view of the defibrillator system of the instant invention with two direct cardiac access electrodes.

The preferred embodiment 2 of the defibrillator system is shown on FIG. 1. Defibrillator 6 is preferably releasably attached to the reference template 10 containing landmark registration elements 4. Direct cardiac access electrode assemblies 8 interface with registration elements 4 to ensure proper positioning and direction of the electrodes with respect to the patient's heart. Reference template 10 further contains apertures 5 and 7 to enable adjustment of registration elements' 4 positions in response to the differences in patients' anatomies. Electrode assemblies 8 are electrically connected to defibrillator 6.

Figure 5:
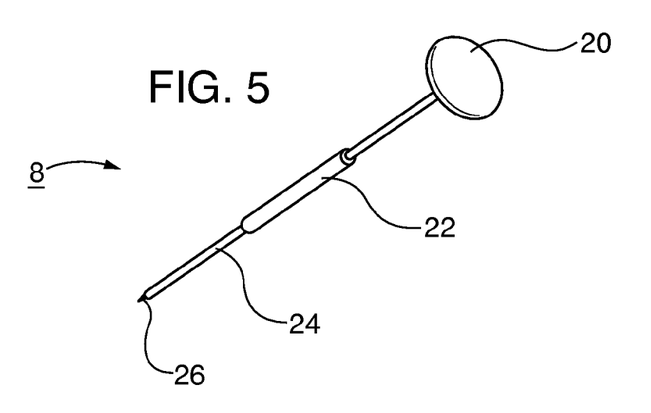
FIG. 5 is a perspective view of a direct cardiac electrode assembly.
Figure 6:
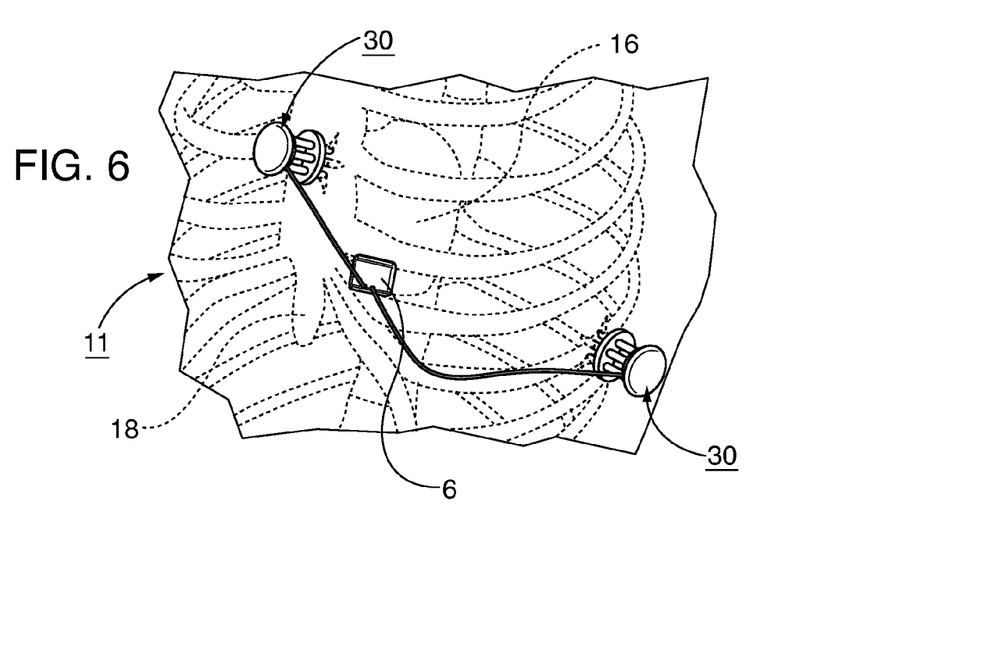
FIG. 6 is a perspective view of the defibrillation system with subcutaneous electrode assemblies positioned on the patient's thorax.
Figure 7:
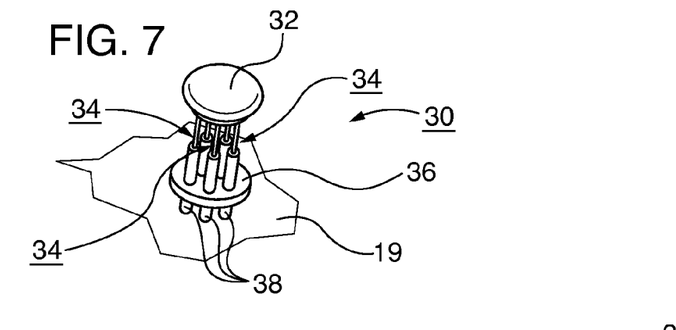
FIG. 7 is a perspective view of the subcutaneous electrode assembly in its pre-deployment configuration.
Figure 8:
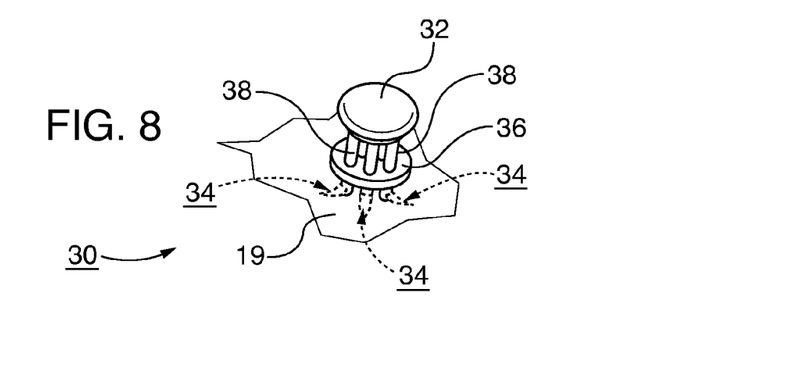
FIG. 8 is a perspective view of the subcutaneous electrode assembly deployed.

As shown on FIG. 5, each direct cardiac access electrode assembly 8 comprises a long conductive needle 26 terminating in a sharp tip, which is covered in its entirety, except for the exposed tip, by electrically insulating layer 24. On the opposite of its sharp tip end, the needle 26 is terminated by a handle 20 used to push the needle into the patient's body prior to defibrillation and to extract it afterwards. The direction of needle's 26 movement is controlled by sleeve 22 interfacing with registration element 4 for precise guidance.

Operation

Figure 2:
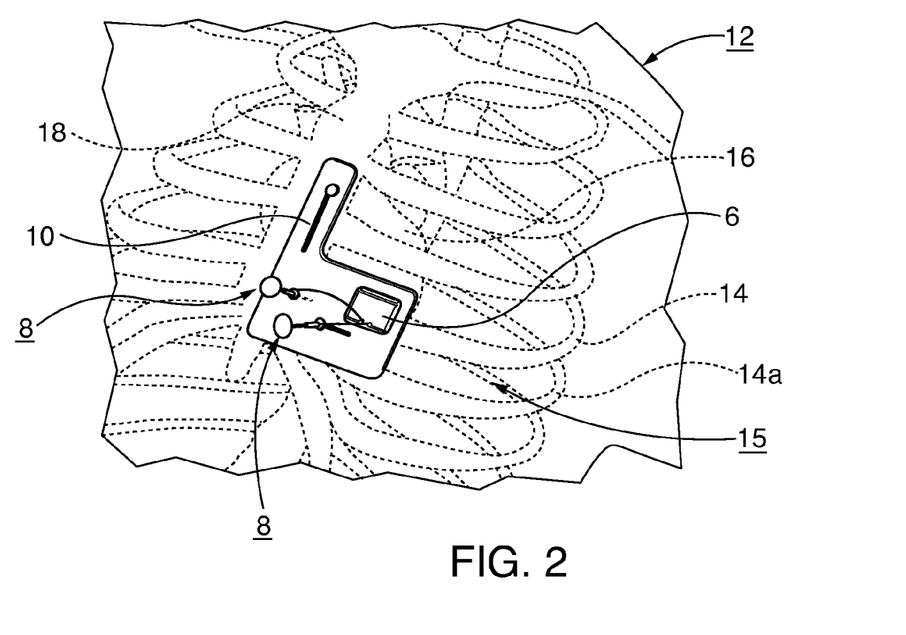
FIG. 2 is a perspective view of the defibrillation system positioned on the patient's thorax and engaging his heart.

Electrode assemblies 8 are kept retracted prior to the operation. Referring to FIG. 2, after adjusting the positions of landmark registration elements 4 according to the patient's anatomy within apertures 5 and 7, reference template 10 is positioned onto patient's upper body 12, with registration elements 4 preferably engaging the body surface immediately over the $3^{rd}$ and $5^{th}$ intercostal spaces and generally parallel to patient's sternum 18.

Electrode assemblies 8 are then pushed into the patient's body preferably via the $5^{th}$ intercostal space 15, between rib 5 denoted 14, and rib 6 denoted 14a, and engage patient's heart 16 with exposed conductive tips of their needles 26. The positioning of the needles 26 is such that they penetrate in the lower margin of the intercostal space in order to avoid contact with veins, arteries and nerves present in the upper margin of intercostal space, on the lower edge of the uppermost rib, in this case, the $5^{th}$ rib.

Defibrillation is then effected by defibrillator 6 generating an electrical pulse of the energy sufficient to defibrillate the patient's heart, which propagates down electrode assemblies 8 to the heart. After defibrillation pulse electrode assemblies 8 are either withdrawn from the patient's body, or a subsequent pulse(s) can be delivered in case the first pulse did not succeed.

Embodiment 2 relies on two-electrode operation where they engage the same or both ventricles, or, by increasing the penetration angle of one of the electrodes, an atrium and a ventricle.

Additional Embodiments

In the foregoing description like components are labeled with like numerals.

Figure 3:
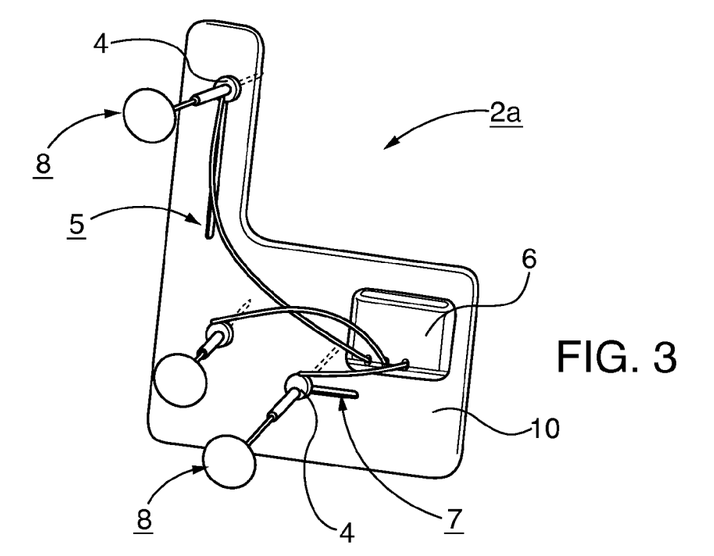
FIG. 3 is a perspective view of the defibrillator system's alternate embodiment with three direct cardiac access electrodes.
Figure 4:
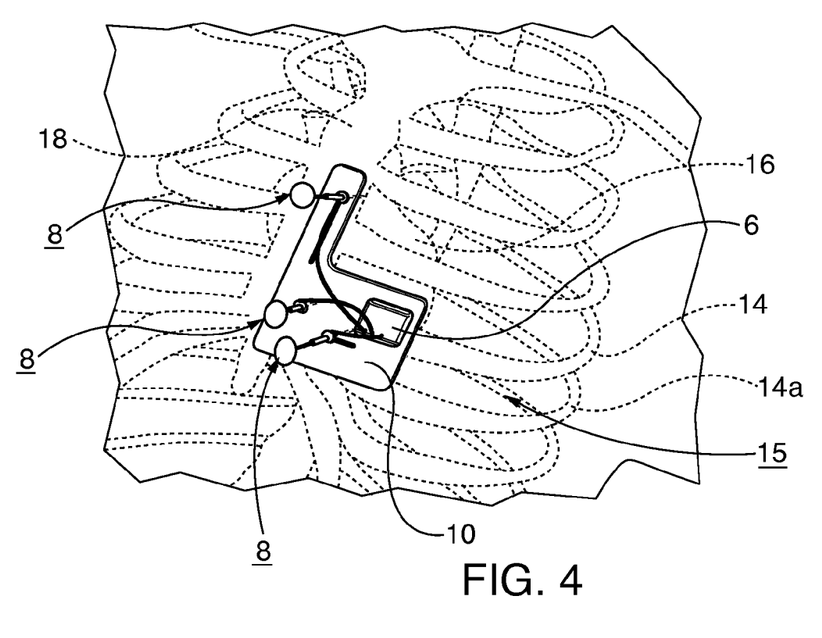
FIG. 4 is a perspective view of the defibrillation system's alternate embodiment positioned on the patient's thorax and engaging his heart.

Referring to FIGS. 3 and 4 an alternative defibrillator system embodiment 2a utilizes a three-electrode defibrillation. This scheme, while more complicated than a two-electrode one, offers flexibility to the defibrillation action. For example, one electrode can engage atrium while two others engage same or both ventricles, or one of them is inserted half-way to serve as a common electrode.

An alternative defibrillator system embodiment 11 utilizing indirect subcutaneous electrode assemblies is shown on FIGS. 6 through 17. On FIG. 6 subcutaneous electrode assemblies 30 are placed onto patient's skin, with their blade electrodes piercing it to establish a low-impedance current path to the heart.

Referring to FIGS. 7, 8, 15, 15a, 16 and 16a subcutaneous electrode assembly 30 comprises several electrode sleeves 38 which contain electrode assemblies 34 contained in a curved inner channel 35 terminating in electrode exit aperture 35a. Each assembly 34 contains one or more flexible blade electrodes 34a connected to the contact pad 34b which in turn is electrically connected to defibrillator 6. Contact pad 34b is also mechanically connected to the deployment handle 32. Flexible electrode's 34a tip is made to be very sharp to facilitate its easy penetration into the skin. Several sleeve-electrode assemblies are held together by plate 36.

Upon placement on the patient's skin 19, handle 32 is pressed downwards toward the skin's surface by the operator. Sleeves 38 internal curved channels 35 terminating in outwardly and radially pointing apertures 35a force blade electrodes 34a to emerge at a slant angle with respect to the skin surface 19, penetrating it. One or more electrodes 34a are thus inserted simultaneously under the skin enabling a low-impedance current path for defibrillation.

Figure 9:
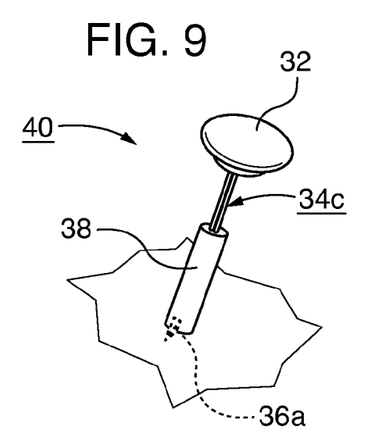
FIG. 9 is a perspective view of the subcutaneous electrode assembly's alternate embodiment in its pre-deployment configuration.
Figure 10:
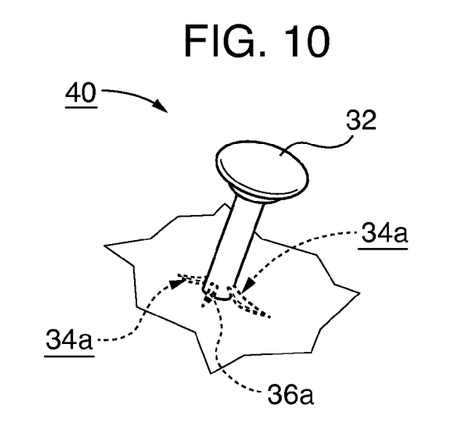
FIG. 10 is a perspective view of the subcutaneous electrode assembly's alternate embodiment while deployed.
Figure 11:
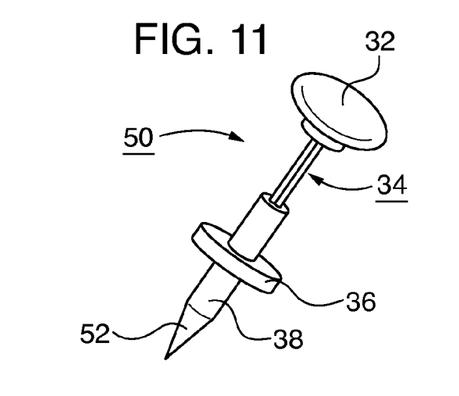
FIG. 11 is a perspective view of a subcutaneous electrode assembly's alternate embodiment in its pre-deployment configuration.
Figure 12:
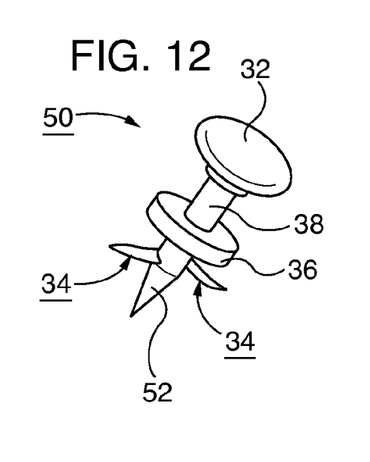
FIG. 12 is a perspective view of a subcutaneous electrode assembly's alternate embodiment while deployed.
Figure 13:
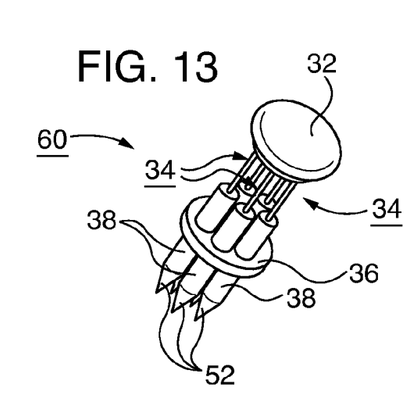
FIG. 13 is a perspective view of another subcutaneous electrode assembly's alternate embodiment in its pre-deployment configuration.
Figure 14:
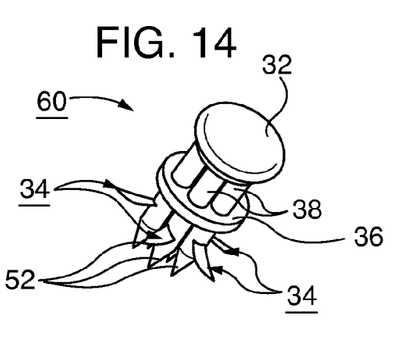
FIG. 14 is a perspective view of another subcutaneous electrode assembly's alternate embodiment while deployed.
Figure 15:
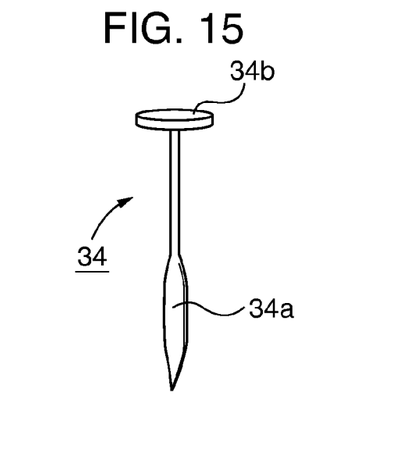
FIG. 15 is a perspective view of a subcutaneous electrode element in pre-deployment configuration.
Figure 15A:
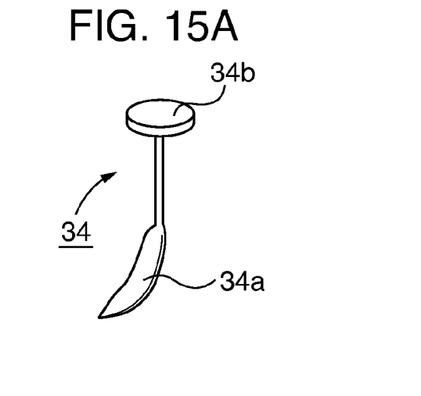
FIG. 15a is a perspective view of a subcutaneous electrode element while deployed.
Figure 16:
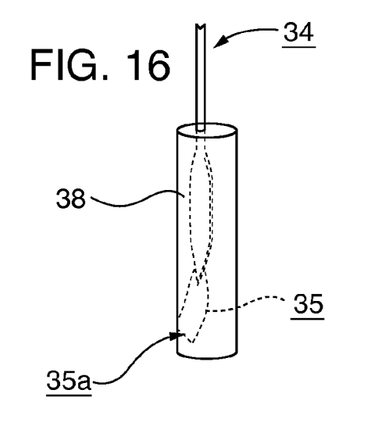
FIG. 16 is a perspective partial view of a subcutaneous electrode assembly in pre-deployment configuration.
Figure 16A:
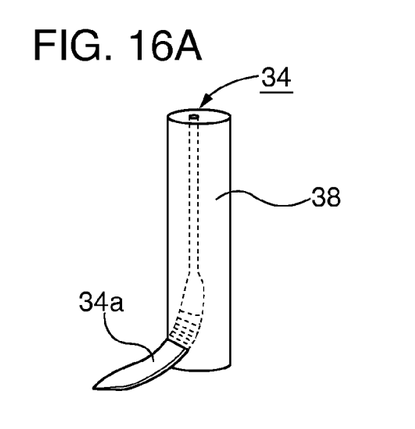
FIG. 16a is a perspective partial view of a subcutaneous electrode assembly while deployed.

FIGS. 9 and 10 show an alternate embodiment of the subcutaneous electrode assembly 40. It is more compact than assembly 30 and utilizes a single sleeve 38 with assembly 34c consisting of two electrodes. To stabilize the assembly on the patient's skin, it is equipped with a rest 36a on its bottom.

Yet another embodiment of the subcutaneous electrode assembly 50 is shown on FIGS. 11 through 14. Instead of the flat bottom of the previous assembly, each sleeve 38 terminates in a sharp tip 52. This construction enables deeper penetration of the skin and subcutaneous layers. The plate 36 serves in this embodiment as a penetration depth limiter.

Figure 17:
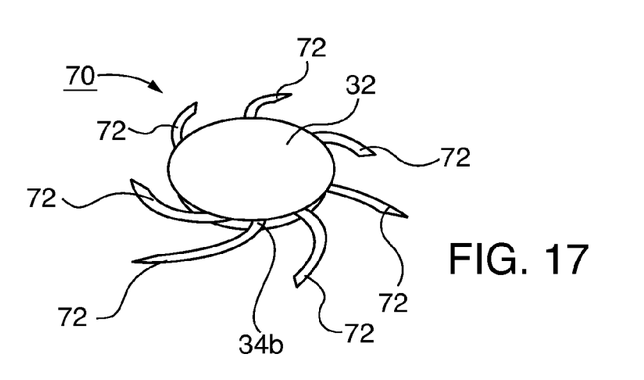
FIG. 17 is a perspective view of a subcutaneous electrode with scimitar-shaped electrode elements.

Another embodiment of the subcutaneous electrode assembly 70 is shown on FIG. 17. It features scimitar-shaped electrodes 72 extending radially from the common contact pad 34b attached to handle 32. The electrodes are inclined to the plane of the handle/contact pad, so when placed on skin 19, they pierce it when handle 32 is turned, in this configuration, clockwise. Rotating handle 32 counter-clockwise removes electrodes 72 from the skin.

Figure 18:
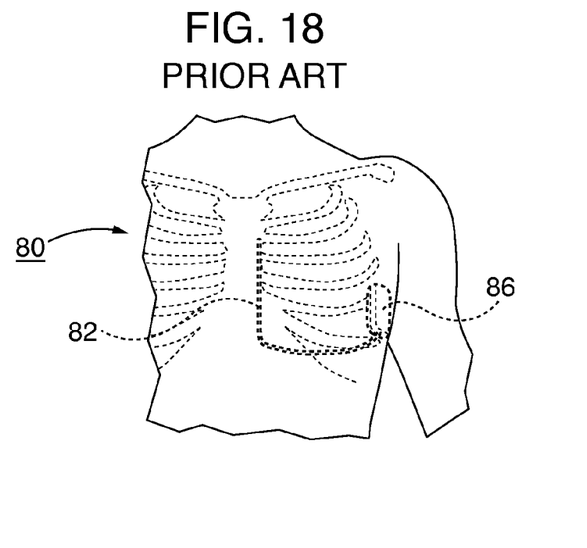
FIG. 18 is prior art of implantable defibrillator with indirect subcutaneous electrode.
Figure 19:
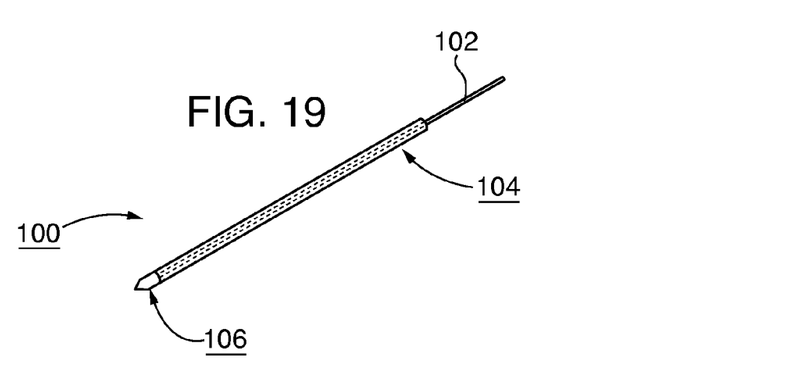
FIG. 19 is a perspective view of a linear subcutaneous electrode assembly inside of the introducer prior to insertion.
Figure 20:
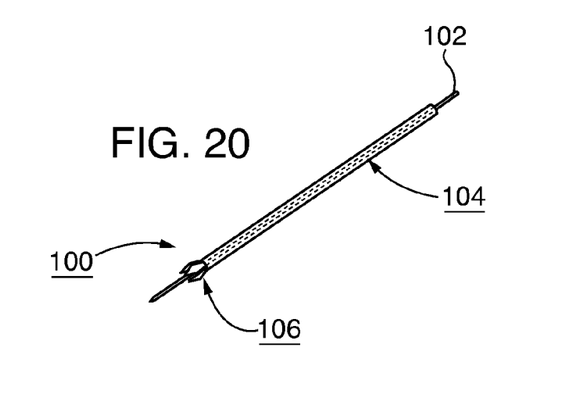
FIG. 20 is a perspective view of a linear subcutaneous electrode assembly inside of the introducer, with introducer being removed.
Figure 21:
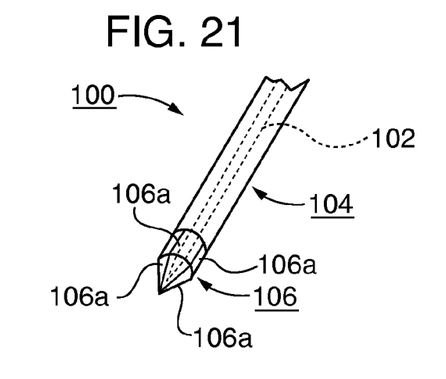
FIG. 21 is a partial perspective view of a linear subcutaneous electrode assembly inside of the introducer, with introducer penetrating tip closed.
Figure 22:
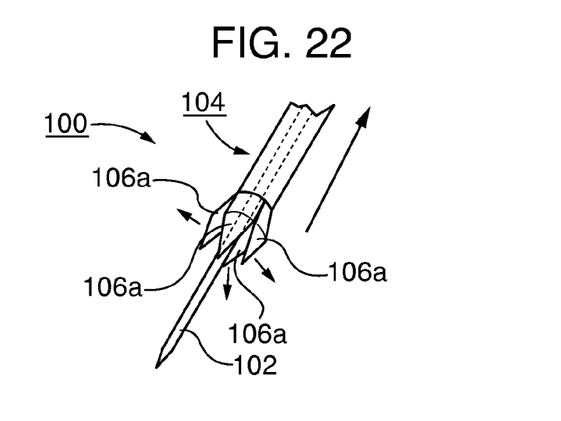
FIG. 22 is a partial perspective view of a linear subcutaneous electrode assembly inside of the introducer, with introducer penetrating tip open while being extracted.
Figure 23:
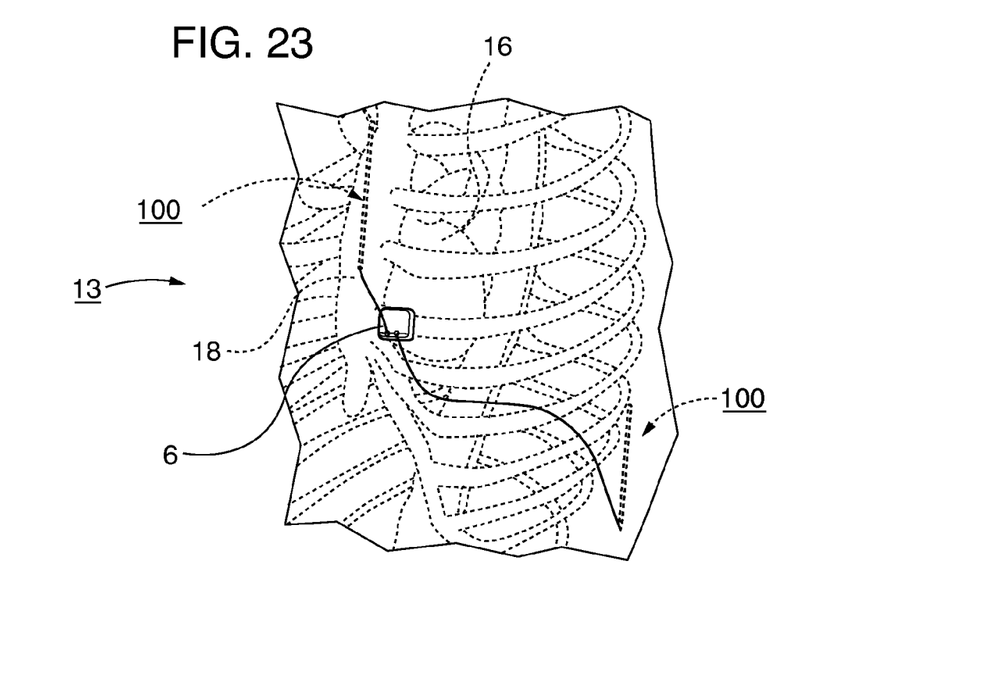
FIG. 23 is a perspective view of the defibrillation system with linear subcutaneous electrode assemblies positioned in the patient's thorax.

Another embodiment of the subcutaneous electrode assembly 100 is shown on FIGS. 19 through 23. A relatively thin and flexible electrode 102 is positioned inside introducer 104 for subcutaneous insertion. Introducer 104 at its distal end has a sharp penetrating tip 106 which consists of several flexible tangs 106a. During insertion tangs 106a are held firmly against each other by skin's resistance, forming a sharp tip 106. Referring to FIG. 23 introducers 104 containing electrodes 102 inside are placed under patient's skin preferably at two locations: one along the sternum 18 and another laterally below left armpit. These locations are customarily selected for external defibrillator electrode pads placement and also shown in the prior art implantable defibrillator system 80 with indirect electrode 82 and implantable defibrillator 86 whose metal case serves as a second electrode, shown on FIG. 18.

When electrode assembly 100 is positioned at the desired position, introducer 104 is withdrawn by the operator's pulling it back off of the electrode 102. During this operation the tip of electrode 102 pushes the tangs 106a of introducer 104 outwards and causes them to flex, clearing electrode 102. Introducer 104 is then slid off the electrode 102, leaving it in place inside patient's body. Upon completion of defibrillation electrode 102 is withdrawn from the patient's body by simple pulling.

Although descriptions provided above contain many specific details, they should not be construed as limiting the scope of the present invention. Several features of distinct embodiments can be combined, for example, the introducer/electrode assembly 100 can be used in the direct cardiac contact embodiments 2 and 2a, with an advantage that a thin electrode can be left in place while chest compressions are performed on the patient as a part of a cardio-pulmonary resuscitation (CPR) procedures.

Thus, the scope of this invention should be determined from the appended claims and their legal equivalents.

I claim:

1. A method for decreasing electrical energy required for external defibrillation of a patient's heart, wherein said method utilizes an external electrical source to apply at least one electrical pulse to said patient's heart, wherein said electrical source is connected to at least two electrodes, namely first electrode and second electrode, wherein said first and said second electrode each are introduced into patient's body deeper than said patient's outer skin layer thereby bypassing electrical impedance of said outer skin layer, wherein said electrodes are capable of forming a closed electrical circuit from said electrical source to said first electrode, through patient's body, through said patient's heart, through patient's body to said second electrode, back to said electrical source, whereby the total electrical impedance of said circuit is reduced by bypassing said outer skin layer and impedance associated therewith, whereby overall electrical energy required for defibrillation of said patient's heart is reduced as a result; wherein said electrodes each comprise at least one electrical conductor element, said conductor capable of penetrating said patient's skin, whereby said conductor is capable of being introduced subcutaneously by a movement substantially perpendicular to surface of said skin; and wherein said conductor is housed in an introducer element, said introducer element assisting in penetration of the patient's skin and subcutaneous positioning of said conductor, said introducer element movable with respect to said conductor to electrically expose said conductor upon completion of subcutaneous placement of said conductor.

2. The method of claim 1, wherein said conductor is capable of being introduced subcutaneously by a movement substantially oblique to surface of said skin.

3. The method of claim 1 wherein more than two of said electrodes penetrate said patient's skin in order to bypass said patient's skin impedance.

4. A method of external cardiac defibrillation wherein at least one electrical pulse is applied directly to the patient's heart, wherein said electrical pulse is generated by an external electrical source, wherein said electrical source is connected to at least two electrodes, wherein each of said electrodes penetrates said patient's body and makes contact with said patient's heart; and further utilizing an electrode alignment template, said template positionable on said patient's body, said template comprising at least one alignment element alignable to at least one landmark on said patient's body, said template interfaceable with said electrodes, said template further controlling position, direction and penetration depth of at least one of said electrodes with respect to said landmark.

5. The method of claim 4 wherein more than two of said electrodes penetrate said patient's body and make contact with said patient's heart.

6. The method of claim 4, wherein each electrode comprises an electrical conductor of essentially elongated shape, said conductor electrically insulated along its length except for its distal tip.

7. The method of claim 4 wherein the position of at least one of said electrodes is adjustable with respect to said alignment element.

8. An external defibrillation system comprising an external electrical source and at least two electrodes connected thereto, whereby said electrodes each penetrate patient's skin in order to bypass said skin's electrical impedance, said electrodes conducting at least one electrical pulse from said electrical source through said patient's heart in order to effect defibrillation of said heart; wherein said electrodes each comprise at least one electrical conductor element, said conductor capable of penetrating said the patient's skin, whereby said conductor is capable of being introduced subcutaneously by a movement substantially perpendicular to surface of said skin; and wherein said conductor is housed in an introducer element, said introducer element assisting penetration of patient's skin and subcutaneous positioning of said conductor, said introducer element movable with respect to said conductor to electrically expose said conductor upon completion of subcutaneous placement of said conductor.

9. An external defibrillation system comprising an electrical source and at least two electrodes connected thereto, wherein said electrodes penetrate patient's body, wherein at least one of said electrodes contacts said patient's heart, said electrodes conducting at least one electrical pulse from said electrical source through said patient's heart; wherein at least one of said electrodes comprises an electrically conductive elongated rod, said electrode electrically insulated along its length except its distal tip, said electrode capable of penetrating patient's body and electrically contacting said patient's heart; and an electrode alignment template, said template positionable on said patient's body, said template comprising at least one alignment element alignable to at least one landmark on said patient's body, said template interfaceable with said electrodes, said template further controlling position, direction and penetration depth of at least one of said electrodes with respect to said landmark.

10. The system of claim 9 wherein more than one of said electrodes penetrate said patient's body and electrically contact said patient's heart.

11. The system of claim 9 wherein the position of at least one of said electrodes is adjustable with respect to said alignment element.

* * * * *